United States Patent [19]

Shim et al.

[11] 4,284,817

[45] Aug. 18, 1981

[54] PROCESS FOR PREPARING THIOPHENOLS

[75] Inventors: Kyung S. Shim, Irvington; Adam E. Skrzec, West Nyack, both of N.Y.

[73] Assignee: Stauffer Chemical Company, Westport, Conn.

[21] Appl. No.: 802,682

[22] Filed: Jun. 2, 1977

[51] Int. Cl.³ .......................................... C07C 149/28
[52] U.S. Cl. ......................................... 568/67; 568/58
[58] Field of Search ............... 260/609 D, 609 E, 670; 568/67, 58

[56] References Cited

U.S. PATENT DOCUMENTS

| | | | |
|---|---|---|---|
| 1,978,069 | 10/1934 | Williams | 260/670 |
| 2,116,182 | 3/1938 | Baur et al. | 260/156 |
| 2,438,838 | 3/1948 | Ballard et al. | 260/609 |
| 2,490,257 | 12/1949 | Crowley et al. | 260/609 D |
| 3,799,989 | 3/1974 | Sherk et al. | 260/609 D |

FOREIGN PATENT DOCUMENTS

| | | | |
|---|---|---|---|
| 45-19046 | 6/1970 | Japan | 260/609 D |
| 46-08293 | 2/1971 | Japan | 260/609 D |

*Primary Examiner*—Donald G. Daus
*Assistant Examiner*—M. C. Eakin
*Attorney, Agent, or Firm*—William C. Gerstenzang

[57] ABSTRACT

Thiophenols are produced by reacting the corresponding benzene compound with hydrogen sulfide in contact with an absorptive catalyst, such as activated carbon, calcined petroleum coke, etc. Temperatures in the range of from about 500° to 900° C. are employed.

12 Claims, 2 Drawing Figures

FIGURE I.

PROCESS FOR PREPARING THIOPHENOLS

BACKGROUND OF THE INVENTION

This invention relates to a process for the production of thiophenol compounds. Such compounds are well-known, having utility as anti-oxidants, polymerization inhibitors, intermediates for the preparation of other chemicals, etc.

Although the thiophenols have been known and used for many years, they remain costly and expensive chemicals. Numerous attempts to prepare these compounds have not resulted in an economical, pollution-free process.

For example, U.S. Pat. No. 2,490,257 discloses the vapor phase reaction of chlorobenzene and hydrogen sulfide in the presence of wood charcoal, while U.S. Pat. No. 3,799,989 teaches a non-catalytic process for preparing thiophenols from the same reactants. Other known methods of preparing thiophenols include the reaction between cyclohexane and sulfur or a sulfur chloride, as described in U.S. Pat. No. 3,671,593, and the reduction of phenylsulfonic acid chlorides with hydrazine.

Attempts to improve upon these prior art processes have recently been disclosed. Thus, U.S. Pat. No. 3,883,599 describes dehydrogenating the corresponding cyclohexylmercaptan by means of $SO_2$ in the gaseous phase in the presence of an inert gas, with a dehydration catalyst. In U.S. Pat. No. 4,006,186, a process is described which comprises reacting a phenylsulfonic acid chloride with hydrazine hydriodic acid and hydrochloric acid to give the corresponding sulfonehydrazide, reacting the product so formed in a second step to provide the corresponding disulfide, reacting the latter material with hydrazine and alkali to form a thiophenolate, and subsequently liberating the thiophenol with a mineral acid.

However, all the prior art processes are subject to disadvantages in that they require costly multi-step methods or result in liberation of chlorine or hydrochloric acid, thus presenting pollution and environmental problems.

SUMMARY OF THE INVENTION

Now it has been found in accordance with this invention that thiophenols can be conveniently prepared from their corresponding benzene compounds in a one-step reaction which obviates the liberation of pollutants.

In the process of this invention, thiophenols are provided by reacting the corresponding benzene compounds with hydrogen sulfide in contact with an absorptive catalyst.

The invention will be better understood by reference to the following description and the accompanying drawings.

DETAILED DESCRIPTION OF THE INVENTION

Figure 1:
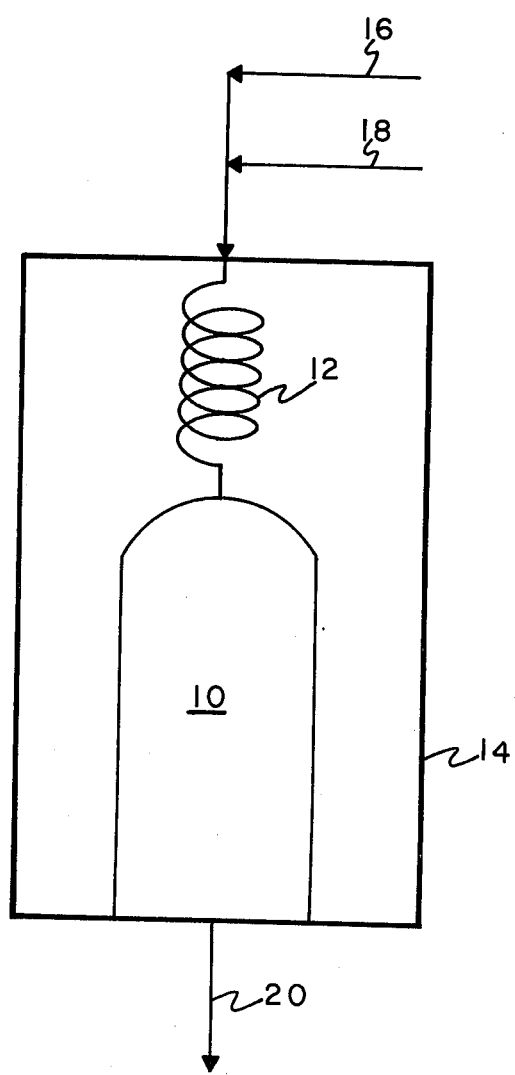
FIG. 1 is a diagrammatic representation of a process in accordance with this invention.

More in detail, the thiophenols produced according to this invention include thiophenol, also known as phenyl mercaptan or phenyl thiol having the empirical formula $C_6H_5SH$, and substituted thiophenols. By the term "substituted thiophenols" in the claims and specification herein is meant thiophenol substituted on the benzene ring with one to five hydroxy, nitro, halogen, alkyl of 1 to 12 carbon atoms or alkoxy of from 1 to 6 carbon atoms, the substituents being identical or the same where more than one substituent is present.

As previously mentioned, one of the reactants in the method of this invention is the benzene compound corresponding to the desired thiophenol. Illustrative benzene compounds suitable for the practice of this invention include benzene, m-cresol, xylene, o-dichlorobenzene, p-dichlorobenzene, nitrobenzene, anisole, p-chlorotoluene, dodecylbenzene, hexylphenol, etc.

As an absorptive catalyst is used a material having a large surface area, in the order of about 1 to about 1000 square meters per gram. Suitable catalysts include active carbons, petroleum coke, various charcoals, calcined petroleum cokes, alumina, clay, silica gel, molecular sieve and various mixtures thereof. Optionally the absorptive catalysts can be admixed with, or impregnated with, co-catalysts such as zinc sulfide, cobalt sulfide, cadmium sulfide, and other transition metal sulfides. Furthermore, various combinations of the aforementioned types of catalysts can be employed, such as mixtures of impregnated catalysts with non-impregnated catalysts, etc. The preferred catalysts are the charcoals and zinc sulfide impregnated charcoals.

The reactants can be employed in stoichiometric amounts, but preferably substantial excesses of hydrogen sulfide are used. Thus, it has been found that a 100% or greater excess of hydrogen sulfide is preferred.

While reaction temperatures from about 500° to about 900° C. can be suitable employed in the practice of this invention, preferably, the reaction is carried out at temperatures from about 600° to about 800° C. Pressure equipment can also be utilized and the reaction can be carried out at a pressure of up to 100 pounds per square inch absolute, and higher.

The reaction is carried out in the gaseous phase in any appropriate apparatus. Product can be recovered after one pass through the absorptive catalyst, or a continuous process wherein off-gas is recirculated can be provided. Two methods suitable for use in the practice of this invention are illustrated in the drawings.

Referring to FIG. 1, 10 represents a static-bed reactor containing an absorptive catalyst. Static-bed reactor 10 is connected to coiled preheating section 12 and both reactor 10 and preheating section 12 are positioned inside electric furnace 14. Hydrogen sulfide gas is fed in through line 16 and the benzene compound through line 18. The mixture of hydrogen sulfide gas and benzene compound is vaporized and preheated in section 12 at temperatures in the range of from about 300° to about 600° C., the specific temperatures being dependent upon the particular benzene compound employed. The gas mixture is then passed through reactor 10 where temperatures of from 500° to about 900° C. are maintained, and product gases leaving through line 20 are condensed to provide the desired thiophenol. Uncondensible by-products can be passed through a caustic scrubber (not shown).

Figure 2:
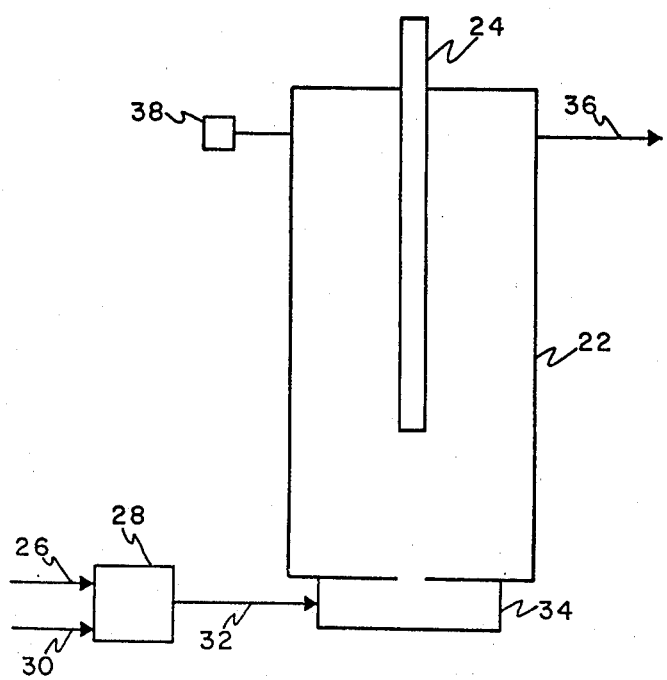
FIG. 2 is a diagrammatic representation of another embodiment of the method of this invention.

Another embodiment of the invention is shown in FIG. 2 wherein an electrothermal fluid-bed reactor is employed. Reactor 22, which contains the absorptive catalyst, is heated by graphite electrode 24, which is powered by a transformer (not shown). Gaseous hydrogen sulfide is fed through line 26 into vaporizer 28 and the benzene compound is fed into vaporizer 28 through line 30. The vaporized mixture is then fed through line 32, which is an electrically traced pipe, into the reactor windbox 34 where it is maintained at a temperature from about 200° to about 250° C., prior to being fed into reactor 22. Windbox 34 is used to equalize the gas pressure in reactor 22. As with the static-bed reactor, a reaction temperature from about 500° to about 900° C. is maintained in the reactor. After passing through reactor 22, product gases leave through line 36 and are condensed to provide the desired thiophenol. A caustic scrubber can be employed to trap uncondensible by-products. Any absorptive catalyst that may be lost by elutriation can be replenished through access port 38.

The following examples will serve to further illustrate the practice of this invention.

EXAMPLE 1

A static-bed reactor as illustrated in FIG. 1 was employed in this example. The reactor 10 consisted of quartz glass 1 inch in diameter and 13 inches long and was attached to a coiled preheating section 12, consisting of ¼ inch diameter quartz tubing, 36 inches long.

The reactor 10 was filled with coal charcoal and heated to 600° C.; the preheater temperature was set at 400° C. Benzene was fed into the preheater at a rate of addition of 0.15 moles per hour and hydrogen sulfide was fed at a rate of 0.28 moles per hour. The reactants were vaporized and heated in the preheater prior to entering the reactor 10.

The gaseous products were quenched in a water cooled condenser and the products identified by comparing gas-liquid chromatography retention times with those of authentic samples of thiophenol and benzene. The liquid condensate contained 3% by weight thiophenol and 97% by weight unreacted benzene.

EXAMPLES 2–4

In these examples, a fluid-bed reactor process as illustrated diagramatically in FIG. 2 was employed. The reactor 22 consisted of a 3 inch, Type 310, stainless steel pipe, 27 inches long, having an expanded section of 5 inch, Type 310 stainless steel pipe, 20 inches long, connected to the top to serve as a disengaging section. Toward the top of the disengaging section, at its side, a ¾ inch coupling was used as access port 38 to make up the bed material that might be lost by elutriation. Directly opposite the access port, a ¾ inch coupling served as the reaction products gas outlet 36.

Flanged to the bottom of the reactor was windbox 34, and sandwiched in between the bottom flange and the windbox was a 1/16 inch thick stainless steel distributor plate with 9-3/32 inch holes on triangular centers. Above the distributor plate, approximately 6 inches of ⅛ inch silica grog is used to protect the distributor plate from the elevated bed temperatures.

Entering through the top reactor flange (Type 310 stainless steel) is a ½ inch diameter graphite electrode 24, carefully located to run through the center line of the reactor. Electrical power is connected to the central electrode from a Westinghouse transformer. Single phase, 60 cycle, alternating current was used in these examples.

The reactants were fed in amounts to provide a 200 mole percent excess of $H_2S$. Benzene was contained in a reservoir made from 4 inch glass pipe with a capacity of 2 gallons. The vaporized feed was transmitted to the reactor windbox 34 through an electrically traced pipe and, to prevent condensation, the windbox was also electrically traced and the gas temperature maintained at 240° C. The feed rate of benzene was metered by a direct reading rotameter. The vaporization rate was maintained constant by adjusting power to the resistance heating elements so that a constant level was maintained in the vaporizer. A temperature of 450°–650° C. was maintained in the reactor.

Reactor product gases leaving the reactor through line 36 passed through a cyclone and entered the glass vertical condenser. The reactor outlet line 36 and cyclone were wound with an electric heating tape to prevent condensation. The product condenser was a standard glass condenser with an estimated 3 square feet of condensing surface. For high condensation efficiency, perchloroethylene was used as a coolant, fed to the condenser at −5° C. The perchloroethylene in turn exchanged with a "Blue M" constant Flow Portable Cooling Unit, set at −19° C. This cooling unit is manufactured by the Blue M. Electric Co., Blue Island, Illinois.

The gases leaving the condenser were burned and conducted to a tall boiler house stack.

Calcined petroleum coke was used as the absorptive material in reactor 22. In the following tables, reaction conditions and weight percent conversion to various products are reported.

|  | EXAMPLE | | |
|---|---|---|---|
|  | 2 | 3 | 4 |
| Temperature °C. | 550 | 600 | 650 |
| Residence time (seconds) | 10.3 | 9.9 | 9.3 |
| Weight % of benzene converted to: |  |  |  |
| Thiophenol | 1.5 | 1.3 | 1.6 |
| Diphenyl Sulfide | 1.8 | 1.2 | 3.9 |
| Biphenyl | 1.6 | 0.7 | 1.7 |

EXAMPLES 5–7

Using the apparatus described in Examples 2–4 but employing BPL activated carbon produced by PPG Industries, Inc. as the absorptive material instead of the calcined petroleum coke, three runs were made. The reaction conditions and results are set forth in the following table.

|  | EXAMPLE | | |
|---|---|---|---|
|  | 5 | 6 | 7 |
| Temperature °C. | 550 | 600 | 650 |
| Residence time (seconds) | 9.8 | 9.3 | 8.5 |
| Weight % of benzene converted to: |  |  |  |
| Thiophenol | 1.0 | 1.3 | 1.4 |
| Diphenyl Sulfide | 0.4 | 0.8 | 1.3 |
| Biphenyl | 1.9 | 1.9 | 1.9 |

EXAMPLES 8–10

In these examples, an absorptive material comprising 67% by weight calcined petroleum coke and 33% by weight zinc sulfide-impregnated activated carbon, was employed. The impregnated activated carbon was made according to conventional techniques by wetting BPL activated carbon from PPG Industries, Inc. with zinc acetate, drying the wet carbon and subsequently passing $H_2S$ through the dried material at 200° C. to convert the zinc acetate to zinc sulfide. The equipment and procedure of the Examples 2-4 were employed; the results are set forth in the table below.

|  | EXAMPLES | | |
|---|---|---|---|
|  | 8 | 9 | 10 |
| Temperature | 550 | 600 | 650 |
| Residence time (seconds) | 10.9 | 10.4 | 9.7 |
| Weight % of benzene converted to: | | | |
| Thiophenol | 1.8 | 1.6 | 1.5 |
| Diphenyl Sulfide | 1.8 | 1.3 | 1.4 |
| Biphenyl | 2.6 | 2.0 | 2.1 |

EXAMPLES 11-13

The absorptive material employed in these examples comprised a mixture of 67% by weight BPL activated carbon and 33% by weight zinc sulfide-impregnated BPL activated carbon, the latter component made as described in Examples 8-10. The equipment and procedure of Examples 2-4 was employed; the results are set forth in the table below.

|  | EXAMPLES | | |
|---|---|---|---|
|  | 11 | 12 | 13 |
| Temperature °C. | 550 | 600 | 650 |
| Residence time (seconds) | 960 | 9.1 | 8.5 |
| Weight % of benzene converted to: | | | |
| Thiophenol | 0.8 | 1.0 | 1.2 |
| Diphenyl Sulfide | 0.2 | 0.4 | 1.4 |
| Biphenyl | 1.2 | 1.7 | 2.3 |

EXAMPLES 14-15

In these examples, the absorptive material comprised 87% by weight calcined petroleum coke mixed with 13% by weight zinc sulfide. The conditions and results obtained using the equipment and procedure of Examples 2-4 are reported in the table below.

|  | EXAMPLE | | |
|---|---|---|---|
|  | 14 | 15 | 16 |
| Temperature °C. | 550 | 600 | 650 |
| Residence time (seconds) | 9.6 | 9.9 | 8.9 |
| Weight % of benzene converted to: | | | |
| Thiophenol | 0.8 | 3.8 | 2.5 |
| Diphenyl Sulfide | 0.7 | 1.4 | 1.8 |
| Biphenyl | 0.4 | 0.7 | 1.1 |

What is claimed is:

1. A process for producing thiophenol which comprises reacting benzene with at least a stoichiometric amount of hydrogen sulfide in contact with an absorptive catalyst having a large surface area.

2. The method of claim 1 wherein said reaction is carried out at a temperature of from about 500° to about 900° C.

3. The method of claim 2 wherein said reaction is carried out at a temperature of from about 600° to about 800° C.

4. The method of claim 1 wherein said absorptive catalyst has a surface area of about 1 to about 1000 square meters per gram.

5. The method of claim 4 wherein said catalyst is charcoal.

6. The method of claim 4 wherein said catalyst is calcined petroleum coke.

7. The method of claim 4 wherein said catalyst is activated carbon.

8. The method of claim 4 wherein at least part of said catalyst is impregnated with a transition metal sulfide co-catalyst.

9. The method of claim 8 wherein said absorptive catalyst comprises a mixture of calcined petroleum coke and zinc sulfide-impregnated activated carbon.

10. The method of claim 8 wherein said absorptive catalyst comprises a mixture of activated carbon and zinc sulfide-impregnated activated carbon.

11. The method of claim 4 wherein said catalyst is admixed with a transition metal sulfide co-catalyst.

12. The method of claim 11 wherein said absorptive catalyst is calcined petroleum coke and said co-catalyst is zinc sulfide.

* * * * *